(12) United States Patent
Abbas et al.

(10) Patent No.: US 6,555,509 B2
(45) Date of Patent: Apr. 29, 2003

(54) MULTI-PHASE TOILET ARTICLES AND METHODS FOR THEIR MANUFACTURE

(75) Inventors: Syed Husain Abbas, Symour, CT (US); Ray Hui, College Point, NY (US); Laurie Ann Coyle, Park Ridge, NJ (US)

(73) Assignee: Unilever Home & Personal Care USA division of Conopco, Inc., Greenwich, CT (US)

(*) Notice: Subject to any disclaimer, the term of this patent is extended or adjusted under 35 U.S.C. 154(b) by 86 days.

(21) Appl. No.: 09/772,019

(22) Filed: Jan. 29, 2001

(65) Prior Publication Data

US 2002/0151453 A1 Oct. 17, 2002

(51) Int. Cl.[7] .................. C11D 13/14; C11D 13/16; C11D 13/18; C11D 17/00; B29C 39/10

(52) U.S. Cl. .................. 510/143; 510/146; 510/447; 510/481; 510/484; 424/401; 264/251; 264/260; 264/271.1; 264/275

(58) Field of Search .................. 510/447, 143, 510/146, 147, 481, 483, 484; 424/401; 264/251, 260, 271.1, 275

(56) References Cited

U.S. PATENT DOCUMENTS

| | | | | |
|---|---|---|---|---|
| 821,245 A | * | 5/1906 | Hutchinson | 401/19 |
| 1,083,571 A | * | 1/1914 | Waltke | 510/133 |
| 1,200,883 A | * | 10/1916 | Scheufler et al. | 510/143 |
| 2,420,734 A | * | 5/1947 | Churchill | 510/143 |
| 2,613,185 A | * | 10/1952 | Marshall | 510/146 |
| 3,479,429 A | | 11/1969 | Morshauser et al. | 424/63 |
| 3,773,672 A | * | 11/1973 | Bredice | 510/143 |
| 4,062,792 A | * | 12/1977 | McNabb | 510/142 |
| 4,202,879 A | | 5/1980 | Shelton | 424/66 |
| 4,277,358 A | * | 7/1981 | Hopkins | 510/143 |
| 4,297,228 A | | 10/1981 | Kamada et al. | 510/142 |
| 4,393,643 A | | 7/1983 | Fryar et al. | 53/471 |
| 4,741,852 A | * | 5/1988 | Ondracek | 510/143 |
| 4,743,443 A | | 5/1988 | Pisani et al. | 424/63 |
| 4,996,000 A | | 2/1991 | Redeker | 510/139 |
| 5,217,639 A | * | 6/1993 | Mottola | 510/146 |
| 5,221,506 A | * | 6/1993 | Dulin | 510/120 |
| 5,602,088 A | * | 2/1997 | Tokosh et al. | 510/144 |
| 5,869,437 A | * | 2/1999 | Wolfersberger | 510/147 |
| 6,136,764 A | * | 10/2000 | Bitton | 510/147 |
| 6,376,441 B1 | * | 4/2002 | Ross et al. | 510/146 |
| 6,383,999 B1 | * | 5/2002 | Coyle et al. | 510/146 |

FOREIGN PATENT DOCUMENTS

| | | | |
|---|---|---|---|
| CA | 835913 | * | 3/1970 |
| FR | 2759902 | | 2/1997 |
| JP | 8060198 | | 3/1996 |
| WO | 01/12772 A1 | | 2/2001 |

OTHER PUBLICATIONS

Michael Maron, *Mojave Magic*, Spring and Summer 2002, QVC.

* cited by examiner

*Primary Examiner*—Lorna M. Douyon
(74) *Attorney, Agent, or Firm*—Alan A. Bornstein

(57) ABSTRACT

A multi-phase solid toilet article whose phases are separated by a membrane, and processes for making the article are described. Each phase is reproducibly fabricated to form an article allowing the user to sequentially or simultaneously derive benefits from the different materials contained in the article's layers. The membrane is either at least partially water soluble or dispersible in the case of a product used with water, or shearable in the case of a cosmetic product which is applied directly to or rubbed on the skin. The membrane material is selected to dissolve or disintegrate with product use, so as to accomplish its intended function of separating the different cosmetic materials until they are consumed. The flowable toilet or cosmetic formulations are simultaneously or separately transferred into the mold, simultaneously or separately allowed to harden, where the membrane divider is not removed and becomes a part of the finished product. The hardened multi-phase article is finally ejected from the mold.

21 Claims, 2 Drawing Sheets

MULTI-PHASE TOILET ARTICLES AND METHODS FOR THEIR MANUFACTURE

BACKGROUND OF THE INVENTION

This invention relates generally to toilet articles, and more particularly to toilet articles having a plurality of layers of different materials separated by at least one pre-formed membrane.

DESCRIPTION OF THE RELATED ART

Solid toilet articles in the form of bars, cakes or sticks have been commercially available for many years. These articles may consist of soaps, detergents, antiperspirants, deodorants, and cosmetics and may contain various other substances such as colouring materials, perfumes, benefiting agents, moisturisers and fillers. Different product formulations are used to accomplish different personal care needs. For example, skin on some parts of the body may be more sensitive than other areas. Some body areas are also more prone to perspire than other areas. In addition, the hands are more often exposed to more hard to remove dirt and grease than the rest of the body. These divergent personal care problems have lead to the production of different toilet articles designed for such different needs. Moreover, various individuals in the household may have different preferences or needs so that the household may keep on hand, at the lavatory or the shower, several different personal care articles.

European Patent Application No. 366209 titled "Method of Production of Tablets of Toilet", published May 2,1990, and U.S. Pat. No. 4,996,000 titled "Multi-Layer Cleansing Bar", issued to Dale R. Redeker on Feb. 26, 1999 both disclose a cast moulded cleansing bar having a plurality of layers of different cleansing materials. U.S. Pat. No. 5,198, 140 titled "Dual Composition Toilet or Detergent Bar Containing Convoluted Surfaces and Tongue and Groove Interlock" issued to David Joshi et al., on Mar. 30, 1993, discloses an extrusion formed dual composition bar. Japanese Patent Kokai Application No. 59-157200, published in Sep. 6,1984, discloses a two phase toilet bar. This two phase bar is made by melt casting a first cleansing composition, removing the first casting from the mold, spraying with coloring pigment, cutting the casting to shape a decorative curve, repositioning the cut first casting in a mold, and casting a second cleansing composition, which adheres to the first cleansing composition layer, to form a two phase bar with a curvilinear boundary layer. U.S. Pat. No. 5,217,639 titled "Dual Phase Toilet Bar Containing a Clear Portion and an Opaque Portion Joined Along a Single Curvilinear Shaped Surface" issued to Nicolas Mottola on Jun. 8, 1993, discloses a dual phase toilet bar. The bar is cast by a sequential molding technique wherein a first molten toilet composition is poured into a plastic mold filing the mold to the 50% mark, allowed to harden, and then a second molten toilet composition is poured into the mold and subsequently allowed to harden. One disadvantage of this molding technique is the variability of the boundary line that is obtained between the two cleansing materials. Japanese Patent Kokai Application No. 08-60198, published in Mar. 5, 1996, discloses a multi-phase toilet bar integrated with adhesives. A disadvantage to making this toilet bar is the complicated production process where the individual phases must be cast, adhesive applied, and then joined together until the adhesive sets.

U.S. Pat. No. 4,202,879 titled "Three Phase Antiperspirant Stick" issued to David Shelton on May 13, 1980, discloses a three phase antiperspirant stick with concentric zones of an antiperspirant and deodorant compositions separated by a shearable wax layer. A disadvantage to making this stick is the complicated production process where the inner phase must be dipped in wax before being cast with the outer phase.

None of the foregoing patents however, disclose a toilet article with multi-layers, each separated by a thin membrane, which is preformed by either solution or dispersion casting, molding, extrusion or other suitable techniques. This membrane may be used to control the shape of each layer reproducibly in a multi-layer toilet article such that the shape of the boundary layer can be custom made and is consistent from article to article. Another potential advantage of the membrane is the separation achieved between the layers such that there is little or no migration of one layer into the other. A distinct drawback of toilet articles that are cast without formed dividers is that they may display random variation with the position of the boundary between the different layers.

SUMMARY OF THE INVENTION

In one aspect, the present invention relates to a multi-layer toilet article containing a plurality of layers of materials, with at least two layers separated by a preformed membrane material. This provides distinct and highly reproducible lines of separation between the layers or phases. In another aspect of the present invention, a multi-layer toilet cleansing bar is provided that functions similarly to conventional toilet bar and its cleansing activity yet can provide skin benefits associated with different cleansing material compositions which are placed in at least two distinct layers of the bar, separated by a preformed membrane. In another aspect of the invention, a multi-layer antiperspirant-deodorant stick is provided that functions similarly to a conventional antiperspirant stick yet can provide skin benefits associated with deodorant or other material compositions which are placed in at least two distinct layers of the stick, separated by a preformed membrane. In another aspect of the invention, a multi-layer cosmetic stick is provided, such as a lipstick or the like, which can incorporate a plurality of colored and/or textured materials which the user may select alone or in combination according to personal preference, and where such a plurality of materials are placed in at least two distinct layers of the cosmetic stick, separated by a preformed membrane.

A further aspect of the present invention is to provide a multi-layer toilet article wherein certain active ingredients are incorporated into one layer but not in the other. The ingredients in one layer may or may not be compatible with the ingredients in an adjacent layer separated by the preformed membrane. A still further aspect of the present invention is to provide a continuous or batch process for manufacturing a multi-layer toilet article wherein a highly reproducible plurality of boundary layers is obtainable, and which remain distinct with use. These and other aspects of the present invention will become more apparent from the detailed description and examples that follow.

DETAILED DESCRIPTION OF THE INVENTION

Figure 1:
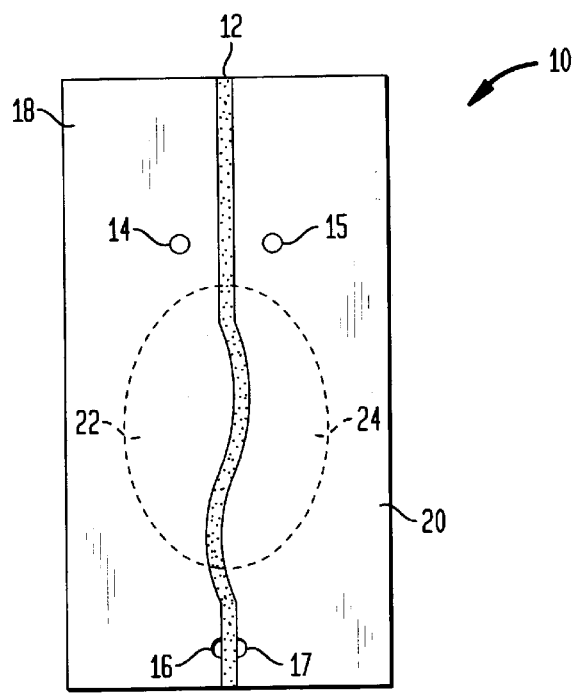
FIG. 1. Is a top planar view of one embodiment of the present invention depicting a closed mold and the membrane positioned between the mold halves.

The inventive solid toilet article comprises at least two adjacent layers, which may be the same or different, and a membrane layer positioned between the layers, for separating and adhesively bonding the adjacent layers. The layers advantageously have a yield stress value from about 20 KPa to about 400 KPa at 25° C. and 50% RH, as measured by art recognized techniques such as with Instron test equipment (Boston, Mass.). Preferably the yield stress value for the layers is in the range of about 100 to about 300 KPa. Preferably the layers each have a similar yield stress value having a maximum difference of about 5 to about 10%.

The membrane is selected from a material that is at least partially water soluble, at least partially water dispersible, a water insoluble, non-thermoplastic, shearable material; and a water insoluble, thermoplastic, shearable material. The membrane may be itself a laminate which is composed of two or more layers with the same or different water solubility, thermal, and physical properties. The membrane may be transparent, translucent, or opaque and may be optionally coated on one or both sides with an adhesive. The membrane may be colored with a dye or pigment and may contain visible particles, stabilizers, fillers, and ancillary components.

A membrane which is at least partially water soluble or dispersible means the membrane will dissolve or disperse as the toilet article, e.g. a cleansing toilet bar, is used with water so that ideally no residual membrane is left protruding from the article as the adjacent phases are consumed. A water insoluble, non-thermoplastic, shearable material means a non-polymeric material which is sufficiently soft to wear away by rubbing, and the like. A water insoluble, thermoplastic, shearable material means a polymeric material which is soft, brittle, or friable when in the form of a thin film and which softens when exposed to heat and returns to its original condition upon cooling.

Suitable materials for such a membrane include naturally derived materials such as water soluble or dispersible cellulosic materials or derivatives thereof such as cellulose ethers like methyl cellulose, hydroxypropyl cellulose, carboxymethyl cellulose, and the like; water soluble or dispersible mono and polysaccharides or derivatives thereof, such as glucose, fructose, alginate, pectin, carrageenan and the like; water soluble or dispersible proteinacious materials or derivatives thereof, such as albumen, gelatin, and the like; and water soluble or dispersible starches, starch hydrolyzates, or derivatives thereof, and the like. Synthetic water soluble or dispersible materials are also suitable such as polyvinyl alcohol, partially hydrolyzed polyvinyl alcohol, vinyl alcohol copolymers, polyvinyl pyrrolidone, polyethylene glycol, acrylic acid-maleic anhydride copolymers, derivatives of the preceding, and blends thereof, and the like.

Alternatively the membrane may be a friable or shearable material such that the membrane disintegrates or is worn away as the toilet article is used e.g. rubbed on the skin. Such materials may include relatively high melting hydrocarbon or silicone waxes such as paraffin, saturated long chain fatty acids, fatty alcohols, glycerides, and the like. Preferably the membrane materials do not lose all their integrity at the processing temperature for making the toilet article in order to prevent the breaching the membrane and therefore the article's phases from mixing with each other. Preferably the membrane materials partially melt or are swelled by the separate phases during the manufacture of the toilet article resulting in better adhesion of adjacent phases with the membrane. Other useful membrane materials include natural and synthetic resins such as shellac or lac, phenolic resins, fatty acids and soaps, derivatives and blends thereof and the like. The combination of the membrane's composition, thickness and its shearability are preferably selected to allow the membrane to disintegrate or wear away at substantially the same rate of wear as the toilet article during use.

Preferably the membrane is preformed from a process selected from solution casting, dispersion casting, molding, extrusion, and other art recognized film forming processes prior to inserting the membrane between at least two adjacent layers of the toilet article.

In the case of where a thermoplastic, shearable material is used, the membrane material is selected so that it adheres to the adjacent layers of the toilet article at the processing temperature for the layers, preferably in the range of about −5 C to about 110 C, more preferably in the range of about 30 to 110C.

Preferably the membrane has a thickness of about 1.5 mm or less, more preferably 1.0 or less. For synthetic water soluble membranes, the prefered thickness is about 0.0025 to about 0.0040 cm. The membrane may be porous, in which case it preferably has a maximum mean pore size of about 0.5 to 1 cm in diameter and a pore density in the range of about 1 to about 100 pores/cm$^2$. Most preferably the porous membrane has a maximum mean pore size of about 0.10 to 0.15 cm in diameter and a pore density in the range of about 10 to about 50 pores/cm$^2$ The optimum pore size will depend on the melt viscosity of the adjacent phases of the toilet article during manufacture. The lower the melt viscosity, the smaller the optimum pore size should be.

The inventive toilet article may be manufactured by a lamination process, casting, injection molding, or any suitable art recognized method for interposing a membrane between two toilet compositions in which the compositions and membrane are adhered together. If a lamination process is used, the desired articles may be stamped or cut from the laminate in any desired shape. Preferably the article is made by casting in a mold where the toilet article layer materials have a melt viscosity in the range of about 10 cps to about 40,000 cps in a temperature range of about −5° C. to 110° C.; most preferably the layer materials have a melt viscosity in the range of about 100 cps to about 3000 cps in a temperature range of about 30° C. to 110° C.

The inventive layered toilet article has at least two layers with the same or different formulations, and includes a cleansing composition, such a toilet bar, a facial cosmetic composition, an antiperspirant composition or a deodorant composition. In one embodiment of the invention, a multiphase toilet bar having a transparent soap formulation and an opaque formulation separated by the membrane may be produced.

In another aspect of the invention, a method for casting a layered toilet article is provided comprising the steps of:
  i. positioning a membrane between a first and a second mold cavity to serve as a barrier in a mold;
  ii. adjusting the mold whereby fluid communication between said first cavity and said second cavity is prevented by said membrane;

iii. transferring simultaneously or sequentially a first flowable material into said first cavity and a second flowable material into said second cavity;

iv. cooling simultaneously or sequentially said first and second flowable materials until they are hardened; and v. removing a hardened, layered article from said mold which incorporates a portion of said membrane.

Preferably, the first and second flowable materials are transferred into the mold at a temperature range of about −5° C. to about 110° C., more preferably at a temperature range of about 30° C. to about 110° C. Preferably the excess membrane is physically trimmed or dissolved in a suitable solvent from the cast article prior or subsequent to casting. The membrane employed in the inventive process has the properties described above.

Description of the Preferred Embodiment

Referring to FIG. 1, this figure illustrates a top planar view of the embodiment of the mold 10 when closed with the membrane 12 positioned between the mold halves 18 and 20, and aligned with locating apertures 34 and locating pins 36. A first molten toilet article phase is poured into left mold cavity 22 via left casting inlet 14 displacing air via left air outlet 16 and a second molten toilet article phase is poured, either simultaneously or sequentially, into right mold cavity 24 via right casting inlet 15 displacing air via right air outlet 17.

Figure 2:
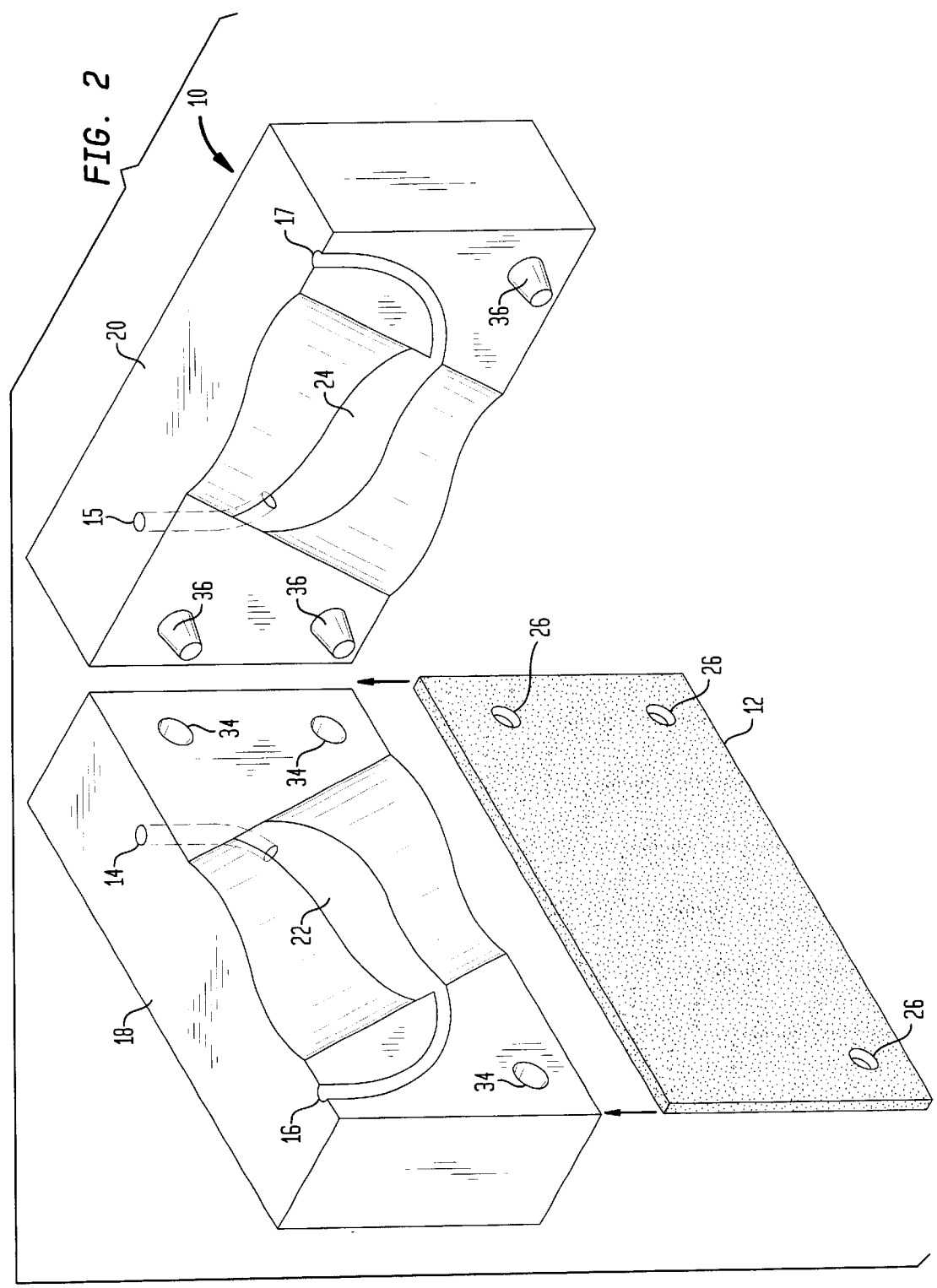
FIG. 2. Is a perspective diagrammatic view of the embodiment depicted in FIG. 1 after the mold is opened with the membrane being received between the mold halves.

Referring to FIG. 2, casting assembly 10 includes a left mold 18, having left mold cavity 22, left casting inlet 14, left air outlet 16 and locating apertures 34, and a corresponding right mold 20, having right mold cavity 24, right casting inlet 15, right air outlet 17, and locating pins 36 which are received into locating apertures 34 when the mold halves are in proper alignment. Also depicted in FIG. 2, is membrane 12 being received into casting assembly 10 via alignment with locating apertures 34 and locating pins 36.

Figure 3:
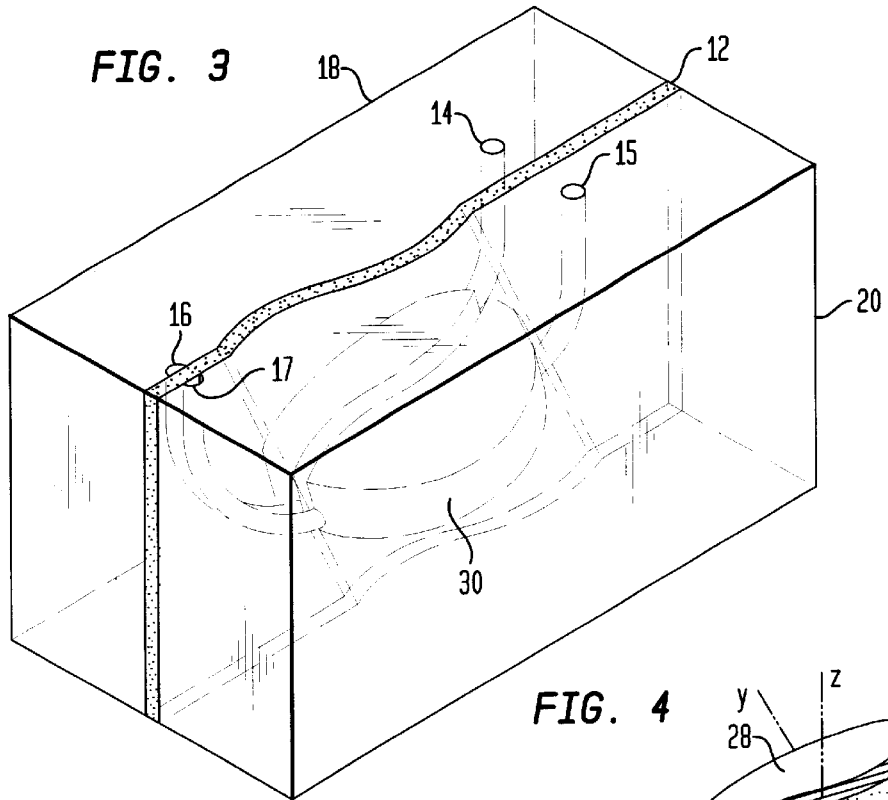
FIG. 3. Is a perspective diagrammatic view of the embodiment depicted in FIG. 1 after the mold is closed with the membrane positioned between the mold halves.

Now referring to FIG. 3, a perspective diagrammatic view of the embodiment depicted in FIG. 1 is illustrated after the mold 10 is closed with the membrane 12 positioned between the mold halves 18 and 20. The left mold cavity 22 and right mold cavity 24 divided by membrane 12 is depicted in broken lines where toilet bar 30 will be formed.

Figure 4:
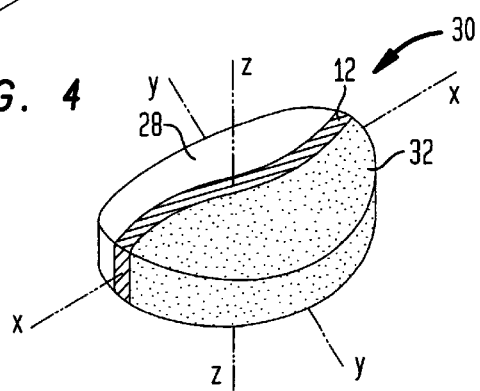
FIG. 4. Is a perspective diagrammatic view of one embodiment of a toilet bar produced by the mold depicted in FIGS. 1 to 3.

Now referring to FIG. 4, a perspective diagrammatic view is depicted of one embodiment of the inventive toilet bar 30 produced by the mold 10 depicted in FIGS. 1 to 3. Toilet bar 30 incorporates a portion of membrane 12 which serves to divide a first phase 28 previously cast in left mold cavity 22 and a second phase 32 previously cast in right mold cavity 24. The excess portion of membrane 12 has been trimmed from the bar. The toilet bar 30 has a major axis along line x—x, a minor axis along line y—y, and a width along line z—z.

Toilet Cleansing Bars

The toilet bar of the present invention may contain one or more transparent, colored, or opaque layers in any combination. Furthermore, the inventive toilet bar may contain layers with the same or different compositions. For good cohesion between adjacent layers and the membrane, the composition of the layers and the non-porous inventive membrane should be compatible with each other. If a porous membrane is used, the composition of the adjacent layers should also be compatible with each other. Usually this is achieved by minimizing the disparity in the adjacent layers formulations or by minimizing the difference in the surface free energy of the adjacent layer formulations. When a subsequent layer is poured, it may flow though the membrane's pores and dissolve part of the previously solidified formulation at the membrane layer's interface and therefore provide good cohesion upon solidification.

The multi-layer toilet bar of the present invention may contain one or more anionic detergents.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

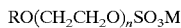

$RO(CH_2CH_2O)_nSO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono-and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$R^4O_2CCH_2CH(SO_3M)CO_2M$;

and amide-MEA sulfosuccinates of the formula;

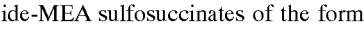

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R^1CON(CH_3)CH_2CO_2M$, wherein $R^1$ ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of at least one layer of the toilet bar. Preferably, this component is present from about 30% to about 60% in the layer.

The acyl isethionate may be an alkoxylated isethionate such as is described in Ilardi et al., U.S. Pat. No. 5,393,466, titled "Fatty Acid Esters of Polyalkoxylated isethonic acid;

issued Feb. 28, 1995; hereby incorporated by reference. This compound has the general formula:

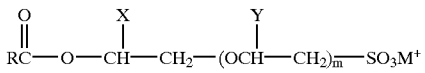

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

At least one layer of the bar may comprise a certain amount of soap as anionic surfactant. When used, the term "soap" is used in its popular sense, i.e., alkalimetal or alkanol ammonium salt of aliphatic alkane or alkene monocarboxylic acids. Sodium, potassium, mono-, di- and tri-ethanol ammonium cations, or combinations thereof, are suitable for purposes of the invention. Generally, sodium soaps are used. Soaps useful herein are the well known alkali metal salts of natural or synthetic aliphatic (alkanoic or alkenoic) acids having 13 to 22 cations, preferably 12 to 18. They may be described as alkali metal carboxylates of acrylic hydrocarbons having about 12 to 22 carbons.

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

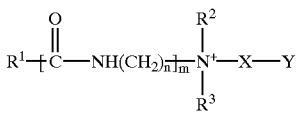

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric surfactants within the above general formula include simple betaines of formula:

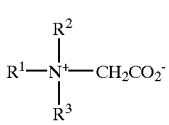

and amido betaines of formula:

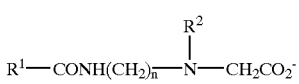

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

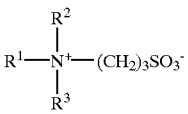

or

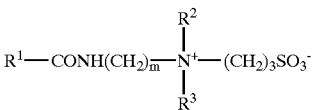

where m is 2 or 3, or variants of these in which —$(CH_2)_3SO_3^-$ is replaced by

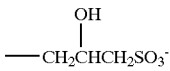

In these formulae $R^1$, $R^2$ and $R^3$ are as discussed previously.

One or more nonionic surfactants may also be used in at least one layer of the toilet bar of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

One or more cationic surfactants may also be used in at least one layer of the inventive multi-layer toilet bar.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar., 27, 1973; and "Surface Active Agents and Detergents" (Vol. I & II) by Schwartz, Perry & Berch, both of which are also incorporated into the subject application by reference.

The inventive multi-layer toilet bar may also contain at least one layer having 10 to 90% by wt., preferably 20 to 80% by wt. of a structurant and/or filler. Such structurant can be used to enhance the bar integrity, improve the processing properties, and enhance desired user sensory profiles.

The structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurant or fillers include starches, preferably water soluble starches such as maltodextrin and polyethylene wax or paraffin wax.

Structuring aids can also be selected from water soluble polymers chemically modified with a hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® 102 (PEG modified glyceryl cocoate, palmate or tallowate) from Rewo Chemicals.

Other structuring aids which may be used include Amerchol Polymer HM 1500 (Nonoxynyl Hydroethyl Cellulose).

In addition, at least one layer of the multi-layer bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2',4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Cationic polymers as conditioners which may be used include Quatrisoft LM-200 Polyquaternium—24, Merquat Plus 3330 —Polyquaternium 39; and Jaguar® type conditioners.

Polyethylene glycols as conditioners which may be used include:

| | |
|---|---|
| Polyox WSR-205 | PEG 14M, |
| Polyox WSR-N-60K | PEG 45M, or |
| Polyox WSR-N-750 | PEG 7M. |

Another ingredient which may be included are exfoliants such as polyoxyethylene beads, walnut shells and apricot seeds, and the like.

Compositions of the multi-layer inventive toilet bar also comprise 1% to 10% by wt., preferably 4% to 7% by wt. water.

In one embodiment of the invention, each layer's composition comprises no more than about 60% surfactant. Said composition also contains 10% to 70% by wt. structurant/filler.

Because of lower surfactant levels, such compositions would be more "drying" on the skin and such compositions would comprise 0.01 to 10% benefit agent/emollient.

The benefit agent "composition" may be a single benefit agent component or it may be a benefit agent compound added via a carrier. Further the benefit agent composition may be a mixture of two or more compounds one or all of which may have a beneficial aspect. In addition, the benefit agent itself may act as a carrier for other components one may wish to add to the bar composition.

The benefit agent can be an "emollient" which is defined as a substance which softens the skin (stratum corneum) by either increasing its water content, adding, or replacing lipids and other skin nutrients; or both, and keeps it soft by retarding the decrease of its water content.

Useful emollients include the following:
(a) silicone oils and modifications thereof such as linear and cyclic polydimethylsiloxanes; amino, alkyl, alkylaryl, and aryl silicone oils;
(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;
(c) waxes such as carnauba, spermaceti, beeswax, lanolin, and derivatives thereof;
(d) hydrophobic plant extracts;
(e) hydrocarbons such as liquid paraffins, vaseline, microcrystalline wax, ceresin, squalene, pristan and mineral oil;
(f) higher fatty acids such as lauric, myristic, palmitic, stearic, behenic, oleic, linoleic, linolenic, lanolic, isostearic, arachidonic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watrercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;
(j) lipids such as cholesterol, ceramides, sucrose esters and pseudo-ceramides as described in European Patent Specification No. 556,957;

(k) vitamins, minerals, and skin nutrients such as vitamins A, E, and K; vitamin alkyl esters, including vitamin C alkyl esters; magnesium, calcium, and milk.

(l) sunscreens such as octyl methoxyl cinnamate (Parsol MCX) and butyl methoxy benzoylmethane (Parsol 1789);

(l) phospholipids;

(m) polyhydric alcohols such as glycerine and propylene glycol; and polyols such as polyethylene glycols, and (n) mixtures of any of the foregoing components, and the like.

A particularly preferred benefit agent is silicone, preferably silicones having a viscosity greater than about 10,000 centipoise. The silicone may be a gum and/or it may be a mixture of silicones. One example is polydimethyl-siloxane having viscosity of about 60,000 centistokes.

The composition may also comprise decorative particulates including speckles, coloured or reflective particles, or shaped particles and the like.

Conventional art recognised cast melt processing techniques may be used to fabricate the inventive multi-layer toilet bar. For example, the melted components of the inventive bar are usually blended together at elevated temperatures. Optionally the water level may be adjusted and the blending will continue. Next an optional drying step may follow whereby the water is reduced. Finally, the molten cleaning composition is poured into molds and cooled to its hardening point. The molds may be made of any rigid material that is not subject to attack by the ingredients of the toilet bar. Mold materials may include plastic, metal, glass, ceramic, or composite materials and the like. Cooling the molten cleansing materials can be accomplished by art recognised cooling techniques including refrigeration, cryogenics, ambient air and the like. Controlled cooling using thermostatic control cooling devices may also be employed.

Conventional art recognised packaging materials may be used to package the inventive multi-layered toilet bar. The package may hold one or more separately packaged bars. The package may also have an optional transparent area to view part or all of the bar contained therein. Paper, plastic, or coated paper, or other flexible or rigid packaging materials that are compatible with the toilet bar may be used. Single layer or laminated packaging material structures may also be used. Preferably, the packaging material is moisture proof, and mold resistant. The packaging material should have good barrier properties to prevent the loss of volatile cleansing composition ingredients such as perfume. Examples, of useful barrier materials are polymer coated paper board or other appropriate materials. Hot melt adhesive or contact adhesive such as glue may be used to adhere a portion of the carton and the wrapper. An appropriate coating would be a low density polyethylene coating and the like.

Cosmetic Sticks having Antiperspirant and Deodorant Properties

Cosmetic sticks having antiperspirant and/or deodorizing effects and based on alcoholic soap gels and/or propylene glycol soap gels are known in the prior art and are described in U.S. Pat. Nos. 2,900,306; 2,857,315; 2,933,433; 3,259,545; 2,970,083; 5,650,142; 4,440,741; 4,322,400; 255,462,736; and 4,382,079 which are here incorporated by reference. The deodorizing agents incorporated into said soap gels include halogenated dihydroxy diphenyl methanes, particularly hexachlorophenes as disclosed in U.S. Pat. Nos. 2,900,306 and 2,970,083 which are here incorporated by reference, and bicarbonates.

In addition to or in lieu of aforesaid deodorants, antiperspirant agents such as sodium zirconium lactate, aluminum hydroxide gel, aluminum chlorhydroxy complex, aluminum hydroxy chloride, sodium aluminum chlorhydroxy lactate complex or mixtures thereof are added to soap gel sticks as disclosed in U.S. Pat. Nos. 2,857,315; 2,933,433; 3,259,545; and 2,970,083 which are here incorporated by reference.

Antiperspirants combat axillary odors by inhibiting perspiration through the action of astringent salts such as aluminum and zinc salts and may be irritating to a considerable number of users. On the other hand, deodorants neutralize the objectionable odors resulting from the degradation of the components of sweat due to chemical and microbial attack into foul smelling fatty acids. Deodorants do not inhibit sweating but rather neutralize the odorous degradation products of sweat, either by their own odorous properties, or by the inhibition of the decomposition action of microbial action on the fats in the sweat residues, or by reaction with the foul smelling fatty acids or by any combination of these mechanisms. Accordingly, they are not as irritating as the antiperspirants.

Depending on the desired end use and desired appeal to consumers, at least one of the compositions that comprise the multi-phase cosmetic stick can include various adjuvents, e.g., fragrances, bacteriocides (such as Triclosan), dyes, sunscreens, other active materials and the like. These adjuvents can include, besides previously mentioned fragrances, bacteriocides and sunscreens, skin conditioners, nail conditioners and the like.

Advantageously, cosmetically active ingredients which dissolve to yield a clear composition may also be included.

Where the composition is to be utilized as a deodorant, preferably the composition includes a fragrance and a bacteriocide. The fragrance illustratively is included in the composition in an amount of 1.0% by weight of the total weight of the composition; and the bacteriocide illustratively is included in the composition in an amount of 0.25% by weight, of the total weight of the composition.

Furthermore, preservatives may also be added. Other various optional components which may be included are described in U.S. Pat. No. 4,759,924 and U.S. Pat. No 5,128,123, the contents of each of which have previously been incorporated herein by reference in their entirety.

The multi-phase cosmetic sticks of the present invention are made by combining the ingredients in liquid or flowable form. Advantageously, heat must be applied in order to provide the ingredients in liquid (melted) form, but pressure injection fabrication techniques or a combination of heat and injection may be used. More volatile components of the composition (e.g., fragrances) should be added near the end of the mixing cycle, and preferably at lower temperatures (while still maintaining the mixture as a liquid), to avoid volatilization of the more volatile components from the mixture. After combining the ingredients, the mixture is poured or pumped into a form having the desired shape (e.g., a stick deodorant package (dispensing container)). The mixture is cooled, so as to solidify.

The multi-phase cosmetic stick composition according to the present invention, after being formed into packaged sticks, is used by the consumer by rubbing the stick on, e.g., the area of the body where application is desired, depositing active materials on the skin surface. Thus, the compositions according to the present invention are utilized by conventional techniques. For example, when utilizing one phase of the compositions according to the present invention as a deodorant stick, having deodorant active materials incorporated therein, the solid stick product is elevated out of the dispensing package and oriented so as to expose this phase, and the properly oriented exposed portion of the stick is then rubbed against, e.g., the axillary region of the human body so as to deposit the deodorant active materials in the axillary region.

Miscellaneous Cosmetics

The multiple phases produced by the present invention may consist of any known lipstick composition and includes those containing additives such as medicaments, flavoring, perfumes, other active ingrdients, and the like. Eye shadow compositions are also usefully produced by the present invention.

The compositions for use in base formulations include any suitable base materials known to the art which contain materials such as carnauba wax, candelilla wax, ozokerite, bees wax, lanolin, ceresin, spermaceti, isopropyl myristate, and castor oil which when combined produce a suitable base formulation having suitable viscosity and physical properties.

The coloring agents usefully employed in the multi-phase inventive compositions to provide proper coloring to the base formulations include those well known to the art such as, for example, organic colors certified for use in drug and cosmetic products, pure inorganic colors, and pure colors of natural origin suitable for use in lipsticks and eye shadow preparatioans. These dyes and pigments include Food, Drug & Cosmetic certified colors and may be added in an amount from about 5 to about 20 parts by weight for each 100 parts by weight of cosmetic base. Flavoring such as synthetic aromatics, essential oils, or other similar material may also be included if desired.

Fortifying agents may also be usefully added to one or more of the cosmetic phases and include materials such as silica, alumina, calcium carbonate, magnesium carbonate, bentonites, talcs, zinc oxide, and the like. Various other agents may also be added to the cosmetic phases to achieve proper molten viscosity such as addition of various oil-soluble resins, soluble metallic soaps, and viscous polymerized oils if heat is used to prepare the inventive cosmetic.

Additional material such as flavoring or perfumes are not necessary to or essential parts of the multi-phase inventive cosmetic masses but may be included as desired in relatively small quantities.

Although the principles of this invention are described to specific cosmetic preparations such as lipsticks and eye shadow preparations, other multi-phase inventive cosmetic products usefully produced herein include molded cosmetic sticks such as eye mascara, and the like. It is also recognized that although the present invention is especially useful in producing cosmetic preparations, it may also be applied in producing non-cosmetic products such as ornamental candles, wax-based pencils, crayons and other drawing materials, and the like without departing from the present invention.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

Two-layer cleansing bars according to the present invention, having a) emollient rich and poor cleansing layers (table 1), b) transparent and opaque cleansing layers (table 2); and c) different colored cleansing layers (table 3) are prepared as follows:

The ingredients for each phase are blended together at a temperature of approximately 90° C. in separate mixing vessels, with continuous mixing. A unitary elastomeric polymer mold as depicted in FIGS. 1–3 having a substantially ovoid shape cavity size at 86 mm along its major axis, 25 mm wide, and 57 mm along its minor axis is used. A 0.1 to 0.2 mm thick, porous water-soluble starch membrane is positioned between the mold halves as depicted in FIGS. 1–3. The membrane has a pore density of 30 to 45 holes/cm$^2$ and the pore diameter varies in the range of about 1.0 to 1.5 mm. The transparent molten mixtures at a temperature of 90° C. are simultaneously poured into both sides of the mold and allowed to air cool to room temperature. The bar is then ejected from the mold, and the excess membrane is removed from the bar by dissolving it in water.

TABLE 1

| Ingredients | Emollient Rich Phase | Emollient Poor Phase |
| --- | --- | --- |
| Sodium Cocoyl Isethionate | 24.00 | 31.00 |
| Stearic acid/Palmitic Acid | 6.00 | 8.00 |
| Alfa Olefin Sulfonate | 7.00 | 8.00 |
| Sodium Lauryl Ether Sulfate (2 EO) | 7.00 | 8.00 |
| Perfume | 1.00 | 1.00 |
| Titanium Dioxide | 1.00 | 1.00 |
| Propylene Glycol | 5.00 | 7.00 |
| Glycerin | 4.00 | 7.00 |
| Lauryl Alcohol | 5.00 | 5.00 |
| 12-hydroxystearic acid | 11.00 | 15.00 |
| Sunflower Seed Oil | 25.00 | 5.00 |
| Water | 4.00 | 4.00 |
| Colorant | 0.001 | — |
| | 100.00 | 100.00 |

TABLE 2

| Ingredient | Transparent Phase | Opaque Phase |
| --- | --- | --- |
| Glycerin | 26.00 | 25.50 |
| Water | 19.50 | 19.50 |
| Sorbitol | 12.00 | 12.00 |
| Coconut Oil | 8.00 | 8.00 |
| Myristic acid | 7.00 | 7.00 |
| Sugar | 7.00 | 7.00 |
| Stearic acid | 6.00 | 6.00 |
| Castor Oil | 5.00 | 5.00 |
| Palmitic acid | 4.00 | 4.00 |
| Sodium Hydroxide | 4.00 | 4.00 |
| Ethyl Alcohol | 1.5 | 1.50 |
| Titanium Dioxide | — | 0.50 |
| Total | 100% | 100% |

TABLE 3

| | White Phase | Pink Phase |
| --- | --- | --- |
| Sodium Coco Isethionate | 39.00 | 39.00 |
| Alfa Olefin sulfonate | 8.00 | 8.00 |
| Sodium Lauryl Ether Sulfate | 8.00 | 8.00 |
| Titanium Dioxide | 1.00 | 1.00 |
| Perfume | 1.00 | 1.00 |
| Propylene Glycol | 6.00 | 6.00 |
| Mineral Oil | 5.00 | 5.00 |
| Sunflower Oil | 3.00 | 3.00 |
| Glycerin | 5.00 | 5.00 |
| 12-Hydroxy Stearic Acid | 12.00 | 12.00 |

TABLE 3-continued

|  | White Phase | Pink Phase |
|---|---|---|
| Hydrogenated Coconut Oil | 7.00 | 7.00 |
| Water | 5.00 | 5.00 |
| Colorant | 0.005 | — |

EXAMPLE 2

The following is an example of a multi-phase inventive preparation of an antiperspirant deodorant cologne stick.

The antiperspirant phase is prepared as follows:

|  | Gms. |
|---|---|
| Part A- |  |
| 40% w./w. sodium aluminum chlorhydroxy lactate in water | 60.00 |
| Water | 6.00 |
| Alcohol (SDA Formula No. 40) | 22.00 |
| Part B |  |
| 70% sorbitol solution N.F. | 3.00 |
| Isopropyl myristate | 1.00 |
| Stearyl alcohol | 1.50 |
| Sodium stearate | 6.50 |

Part A is heated to 60° C. and Part B is then added and the mixture heated with agitation (without loss of alcohol) until clear. The mixture is poured at 60° C. into one half of a cylindrical mold of suitable size, i.e., ¾inch in diameter, divided by a shearable paraffin membrane having a thickness of 1 to 1.5 mm.

The deodorant stick phase is prepared as follows:

|  | Gms. |
|---|---|
| Alcohol (SDA No. 40) | 83.00 |
| Sodium stearate | 7.00 |
| Hexachlorophene | 0.50 |
| Water | 5.00 |
| Propylene glycol | 3.00 |
| Perfume compound | 1.50 |

All ingredients are heated together with agitation in a closed vessel fitted with a reflux condenser until clear. The mixture is poured at 65° to 70° C. into the second half of the mold containing part A. The material is removed from the mold when cool. The resulting solid stick comprises the unperfumed antiperspirant phase and the deodorant cologne stick phase separated by the shearable paraffin membrane. The excess paraffin membrane is physically trimmed away.

EXAMPLE 3

An example of a suitable lipstick base (Table 4) and eye shadow (Table 5) composition usefully employed herein is as follows:

TABLE 4

| Composition | Weight percent |
|---|---|
| Partially hydrogenated Castor oil | 64 |
| Candelilla wax | 7 |

TABLE 4-continued

| Composition | Weight percent |
|---|---|
| Lanolin | 10 |
| Carnauba wax | 3 |
| Ozokerite | 3 |
| Bees wax | 7 |
| Isopropyl myristate | 5 |
| Color A | 0.5 |
| Color B | 0.5 |

TABLE 5

| Composition | Weight percent |
|---|---|
| Ceresin wax, M.P. 67° C. | 31.0 |
| Hydrogenated cottonseed oil | 6.0 |
| Partially hydrogenated Castor oil, U.S.P. | 50.0 |
| Carnauba wax | 4.0 |
| Mineral oil | 7.0 |
| Butylated hydroxy anisol | 0.1 |
| Cab-o-sil[1] | 0.9 |
| Color A | 0.5 |
| Color B | 0.5 |

The solid lipstick and eye shadow compositions described in Tables 4 and 5 are separately blended and heated until molten. The mixtures of lipstick having different colors or eye shadow having different colors are then poured simultaneously into a suitably shaped mold divided by a preformed paraffin membrane having a thickness of approximately 1.0 to 1.5 mm. The solid multi-phase cosmetic is removed from the mold when cooled to room temperature and the excess paraffin membrane is trimmed with a suitable cutting tool.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A solid toilet cleansing or cosmetic article, comprising: at least two layers, and a preformed membrane layer positioned therebetween for separating and adhesively bonding said layers; wherein said layers may be the same or different; and wherein the at least two layers are opaque;

each of said layers having a yield stress value from about 20 KPa to about 400 KPa at 25° C. and 50% RH;

said membrane is selected from a material that is at least partially water-soluble, at least partially water-dispersible, a water insoluble, non-thermoplastic, shearable material; and a water insoluble, thermoplastic, shearable material; said membrane being worn away as the toilet article is used; and said membrane is formed from a process selected from solution casting, dispersion casting, molding and extrusion prior to inserting said membrane between said layers; and said non-thermoplastic shearable material is selected from hydrocarbon or silicone waxes, natural and synthetic resins, and derivatives and blends thereof.

2. The article of claim 1 wherein said thermoplastic, shearable material adheres to said layers at the processing temperature for said layers.

3. The article of claim 2 wherein said temperature is in the range of about −5° C. to about 110° C.

4. The article of claim 1 wherein said membrane has a thickness of about 1.5 mm or less.

5. The article of claim 1 wherein said membrane is porous.

6. The article of claim 5 wherein said membrane has a maximum mean pore size of about 1 cm and a pore density in the range of about 1 to about 100 pores/cm$^2$.

7. The article of claim 1 wherein said membrane's composition includes a material selected from cellulose, monosaccharide, polysaccharide, starch, polyvinyl alcohol, partially hydrolyzed polyvinyl alcohol, polyvinyl pyrrolidone, polyethylene glycol, acrylic acid-maleic anhydride copolymers, and salts, derivatives, and blends thereof.

8. The article of claim 1 wherein said at least two layers has a melt viscosity of about 10 cps to about 40,000 cps in a temperature range of about −5° C. to 110° C.

9. The article of claim 1 wherein one of said two layers includes a cleansing composition, a cosmetic composition, an antiperspirant composition or a deodorant composition.

10. A method for casting a layered toilet article comprising the steps of:
    i. positioning a membrane between a first and a second mold cavity to serve as a barrier in a mold;
    ii. adjusting the mold whereby fluid communication between said first cavity and said second cavity is prevented by said membrane;
    iii. transferring simultaneously or sequentially a first flowable material into said first cavity and a second flowable material into said second cavity;
    iv. cooling simultaneously or sequentially said first and second flowable materials until they are hardened; and
    v. removing a hardened, layered article from said mold which incorporates a portion of said membrane; wherein at least the first and second flowable materials are opaque; and.
    vi. wherein said membrane is selected from a material that is at least partially water soluble, at least partially water dispersible, a water insoluble, non-thermoplastic, shearable material; and a water insoluble, thermoplastic, shearable material; said shearable material being worn away as the toilet article is used; and said non-thermoplastic shearable material is selected from hydrocarbon or silicone waxes, natural and synthetic resins, fatty acids and soaps, derivatives and blends thereof.

11. The method of claim 10 further comprising trimming excess membrane from said article.

12. The method of claim 10 wherein said first and second flowable material are transferred into said mold at a temperature range of about −5° C. to about 110° C.

13. The method of claim 12 wherein said thermoplastic, shearable material adheres to said layers at the processing temperature for said layers.

14. The method of claim 13 wherein said temperature is in the range of about −5° C. to about 110° C.

15. The method of claim 10 wherein said membrane has a thickness of about 1.5 mm or less.

16. The method of claim 10 wherein said membrane is porous.

17. The method of claim 16 wherein said membrane has a maximum mean pore size of about 1 cm and a pore density in the range of about 1 to about 100 pores/cm$^2$.

18. The method of claim 10 wherein said membrane's composition includes a material selected from cellulose, monosaccharide, polysaccharide, starch, natural resin, hydrocarbon wax, fatty acid, polyvinyl alcohol, partially hydrolyzed polyvinyl alcohol, and salts, derivatives, and blends thereof.

19. The method of claim 10 wherein said at least two layers has a melt viscosity of about 10 cps to about 40,000 cps in a temperature range of about −5° C. to 110° C.

20. The method of claim 10 wherein said at least one of said two layers include a cleansing composition, a cosmetic composition, an antiperspirant composition or a deodorant composition.

21. The method of claim 10 further comprising at least two layers of the same or of different formulations.

* * * * *